United States Patent [19]

Avery

[11] 4,167,877
[45] Sep. 18, 1979

[54] METHOD AND INSTRUMENT FOR VIBRATION ANALYSIS

[76] Inventor: Hazelton H. Avery, 1202 W. Galena Blvd., Aurora, Ill. 60506

[21] Appl. No.: 907,024

[22] Filed: May 17, 1978

[51] Int. Cl.² ............................................. G01N 29/00
[52] U.S. Cl. ...................................... 73/579; 73/662; 73/665
[58] Field of Search ................. 73/579, 580, 581, 582, 73/583, 652, 662, 665, 671, 466, 467

[56] References Cited

U.S. PATENT DOCUMENTS

| 2,557,659 | 6/1951 | Ingraham | 73/467 |
| 3,762,225 | 10/1973 | Müller | 73/466 |
| 3,987,338 | 10/1976 | Puetz | 73/466 |

*Primary Examiner*—Anthony V. Ciarlante
*Attorney, Agent, or Firm*—Edward C. Threedy

[57] ABSTRACT

A method for visually indicating the natural frequencies of a vibrating member utilizing an improved instrument strobed through suitable frequency pick-ups such as accelerometers indiscriminately placed on the vibrating structure to be analyzed.

1 Claim, 2 Drawing Figures

U.S. Patent
Sep. 18, 1979
4,167,877
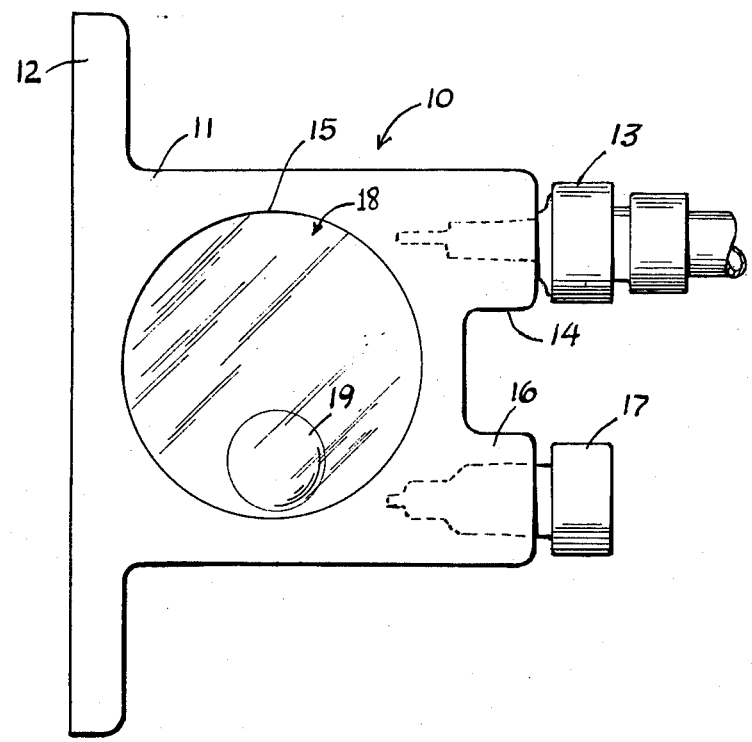
FIG. I.
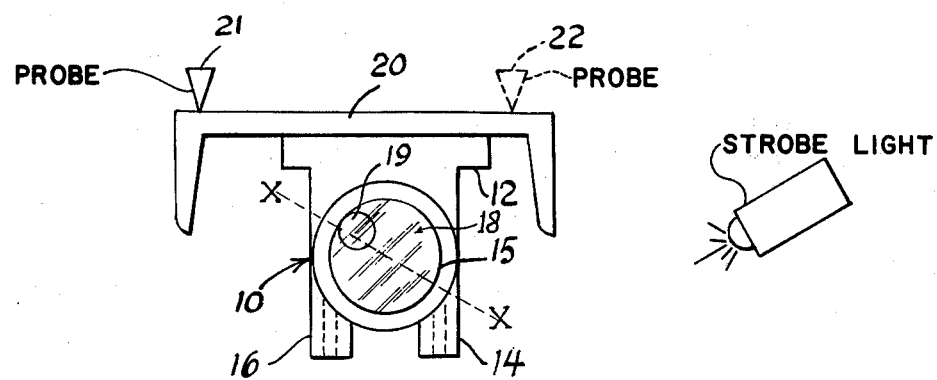
FIG. 2.

METHOD AND INSTRUMENT FOR VIBRATION ANALYSIS

SUMMARY OF THE INVENTION

The present invention includes a vibration generator of the ball or roller type adapted to be fastened to a member to be analyzed and in which the ball or roller is strobed through suitable frequency pick-ups with the strobed ball or roller visually displayed in a locked-in clocked position within the vibration generator.

It is the behavior of the strobed vibrator element that reveals the nature of the vibrating structure. The strobed vibrating element as observed within the vibrating instrument will lock in or appear frozen in a clocked position representing the natural frequencies of a vibrating member of the structure.

The vibrating instrument may be either of a pneumatically actuated ball or roller type having a transparent cover through which the vibrating element is strobed so as to indicate a clocked position responsive to the resonant frequencies of the vibrating member.

This invention will provide an instrument in the form of a vibration generator and a method to indicate the natural frequency of a vibrating member.

The method includes strobing an indicator in a clocked position which is responsive to the natural frequencies of the vibrating member.

In the situations where the structure to be analyzed is made up of a plurality of parts each will have its own natural frequency which can be visually clocked on the instrument. As each part of the structure has its resonant frequency altered the remaining vibrating part or parts will cause the indicator to shift to a new strobed clocked position indicating a change in the vibrating frequency of the structure. Thus if any resonanting member is altered the clocked frequency changes and the indicator will immediately reposition itself into a new clocked position which represents a different or additional vibrations at their natural frequencies. It has been determined that the change from a first strobed clocked position of a resonating member will upon alteration lock into a new clocked position 180° from the original clocked position.

It is an object of this invention to induce a small amplitude vibration to a specimen and zero in on its reaction to a specific frequency range to eliminate any and all resonant frequencies which are detected by the instrument.

DESCRIPTION OF THE DRAWINGS

The invention will be best understood by reference to the accompanying drawing showing the preferred form of construction by which the objects of the invention are achieved and in which FIG. 1 is a side elevational view of the vibration generator of this invention, and FIG. 2 is a schematic view showing the instrument in a functional operation.

GENERAL DESCRIPTION

FIG. 1 shows a vibration generator 10 which includes a housing 11 providing a flat mounting flange 12 at one end thereof. The housing 11 is adapted to receive a suitable nozzle 13 adapted to have open communication through one leg 14 of the housing 11 with an interior well 15. Extending through a second leg 16 is the exhaust port 17 which likewise has open communication with the interior well 15. Adapted to cover one side of the well 15 is a transparent cover 18 through which a movable vibrating member 19 is visible.

The vibrating member 19 as shown in FIG. 1 constitutes a metallic ball. However, without changing the function and operation the housing 11 could be constructed to include a vibrating member in the form of a roller.

The vibrating member operates in the same manner as that shown in U.S. Pat. No. 2,917,290 dated Dec. 15, 1959. As such an introduction of an activating force through the nipple 13 will cause the vibrating member 19 to spin about the periphery of the well 15. It is this action that imparts vibrating motion through the flange 12 onto any structure secured thereto.

FIG. 2 discloses the instrument of FIG. 1 in an operative position wherein the flange 12 has been secured to a structure 20 which is to be subject to vibration analysis.

As shown in FIG. 2 a vibration pick-up 21 is employed which comprises a basic accelerometer which is of a type readily available and as indicated in U.S. Pat. No. 2,802,145 is well known in the art. The pick-up 21 as shown in FIG. 2 will measure resonant frequencies of the structure 20 as it is caused to vibrate through the actuation of the vibration generator 10.

The pick-up 21 is connected to a strobe light so that the same will be ignited through a signal generated by the resonance of the vibrating structure 20. With the strobe light position adjacent to the transparent cover 18 of the vibration generator 10 the activated vibrating element 19 will be strobed so as to appear in a static or locked-in position which is termed as being clocked. In the illustration of FIG. 2 the clocked position of the strobed vibrating member 19 is at 10:30.

The method of vibration analysis through the instrument described is to utilize a vibration generator having a transparent cover by which the vibrating element may be strobed. The strobed element reveals a clocked position and as in the case of FIG. 2 it represents a clocked position of 10:30. This position falls on an axis X—X which extends through the centerpoint of the well 15 as well as through the diameter of the vibrating element 19. This axis X—X indicates that the structure 20 is being displaced through vibration in that direction. If the operator would place the pick-up 21 in the dotted line position 22 on the structure 20, and visually record the same clocked position, to-wit: 10:30, it would indicate that the structure 20 is being displaced along an axis which is parallel to the axis X—X.

If, however, the clocked position 22 of the pick-up 21 is 180° from that of the prior clocked position of the pick-up, to-wit: 4:30, then it would indicate that the displacement of structure 20 is one in torsion. This would indicate that the point under pick-up 21 would go up while the point under pick-up position 22 goes down. Thus, it is apparent that the instrument and method of vibration analysis permits the obtaining of various forms of vibrational behavior in any structure being tested.

From the foregoing it is apparent that the instrument and method of its use as described provides a vibration generator which easily locks onto a frequency which is equal to the natural frequency or one of its harmonic modes of a single component making up but one part of a combination of components, or a part made up from a combination of partial members.

By strobing the vibrating element of the vibrator it has been shown that the same will freeze at a discreet clocked position when a single member of the entire structure vibrates at its natural frequency or at one of its harmonic modes. This particular vibrating member can be easily found simply by touching or reinforcing the member resonating and thus alter its resonating character. This change will immediately cause the vibrating element to jump from the previous locked-in frequency position to a new frequency clocked position, which represents another component vibrating at its natural frequency. This process can be continued such that the next member and its frequency can be easily located.

By the use of the instrument and the method described, once a member or combination of members is located that is resonating, the clocked position of the vibrating element in the instrument that is strobed can be used as a reference to show how that member or combination is vibrating and how it can be braced to change its stiffness within the structure and thus change its frequency response.

While I have illustrated and described the preferred form of construction for carrying my invention into effect, this is capable of variation and modification without departing from the spirit of the invention. I, therefore, do not wish to be limited to the precise details of construction as set forth, but desire to avail myself of such variations and modifications as come within the scope of the appended claims.

Having thus described my invention what I claim as new and desired to protect by Letters Patent is:

1. An instrument for inducing vibrations onto a structural member to be analyzed including a housing for a single mass vibration-inducing element and comprising:
   (a) means within said housing through which said vibration-inducing element is free to move,
   (b) a transparent cover for one side of said means through which said movable vibration-inducing element is exposed,
   (c) means for freely moving said vibration-inducing element through a single thin plane within said means within said housing, and
   (d) strobscopic means for visually indicating one position of said moving vibration-inducing element within said means within said housing so as to visually establish a reference line extending through the center of said strobed vibration-inducing element and the center of its rotational movement.

* * * * *